(12) United States Patent
Gessner et al.

(10) Patent No.: US 8,710,225 B2
(45) Date of Patent: Apr. 29, 2014

(54) THIOCYANATO OR ISOTHIOCYANATO SUBSTITUTED NAPHTHALENE DIIMIDE AND RYLENE DIIMIDE COMPOUNDS AND THEIR USE AS N-TYPE SEMICONDUCTORS

(75) Inventors: Thomas Gessner, Heidelberg (DE); Helmut Reichelt, Neustadt (DE); Nicolle Langer, Heppenheim (NL); Anke Schwind, Ransweiler (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/978,830

(22) PCT Filed: Jan. 10, 2012

(86) PCT No.: PCT/IB2012/050121
§ 371 (c)(1),
(2), (4) Date: Jul. 9, 2013

(87) PCT Pub. No.: WO2012/095790
PCT Pub. Date: Jul. 19, 2012

(65) Prior Publication Data
US 2013/0289279 A1    Oct. 31, 2013

Related U.S. Application Data

(60) Provisional application No. 61/431,067, filed on Jan. 10, 2011.

(51) Int. Cl.
*C07D 471/08* (2006.01)
*H01L 51/50* (2006.01)

(52) U.S. Cl.
USPC .............. 546/37; 313/496; 257/40; 546/66; 546/26

(58) Field of Classification Search
USPC ................ 546/37, 66, 26; 313/498; 257/40
See application file for complete search history.

(56) References Cited

U.S. PATENT DOCUMENTS

| | | | |
|---|---|---|---|
| 8,404,844 B2 * | 3/2013 | Kastler et al. | 546/37 |
| 2006/0202195 A1 | 9/2006 | Marks et al. | |
| 2007/0181961 A1 | 8/2007 | Marks et al. | |
| 2007/0259475 A1 | 11/2007 | Konemann et al. | |
| 2010/0319778 A1 | 12/2010 | Kastler et al. | |

FOREIGN PATENT DOCUMENTS

| | | |
|---|---|---|
| DE | 195 47 209 A1 | 6/1997 |
| WO | WO 2009/098252 A1 | 8/2009 |
| WO | WO 2010/006698 A1 | 1/2010 |

OTHER PUBLICATIONS

International Search Report issued May 3, 2012 in PCT/IB2012/050121.
John A. Dean, Ed. Lange's Handbook of Chemistry, 13$^{th}$ Ed., McGraw Hill Book Company, 1985, translated by Shang J F et al. Science Press, Mar. 1993, Chapter 3, 7 pages (p. 3-134, table 3-12).
Brooks A. Jones, et al., "Tuning Orbital Energetics in Arylene Diimide Semiconductors. Materials Design for Ambient Stability of n-Type Charge Transport", J. Am. Chem. Soc. Nov. 14, 2007, vol. 129, pp. 15259-15278.

* cited by examiner

*Primary Examiner* — Charanjit Aulakh
(74) *Attorney, Agent, or Firm* — Oblon, Spivak, McClelland, Maier & Neustadt, L.L.P.

(57) ABSTRACT

Disclosed are thiocyanato or isothiocyanato substituted naphthalene diimide and rylene diimide compounds according to formula (I), use of these compounds as n-type semiconductors, methods of preparing these compounds, as well as various compositions, composites, and devices that incorporate these compounds.

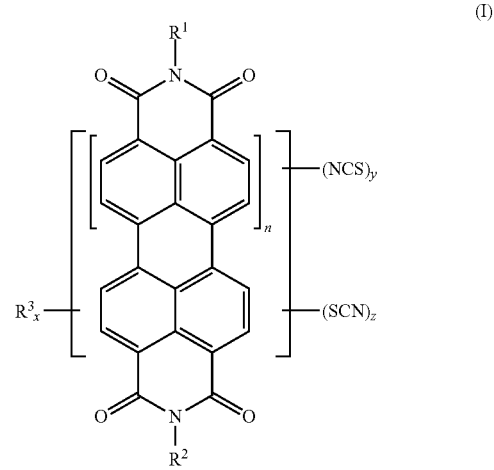

15 Claims, 4 Drawing Sheets

Figure 2a
Figure 2b
Figure 2c
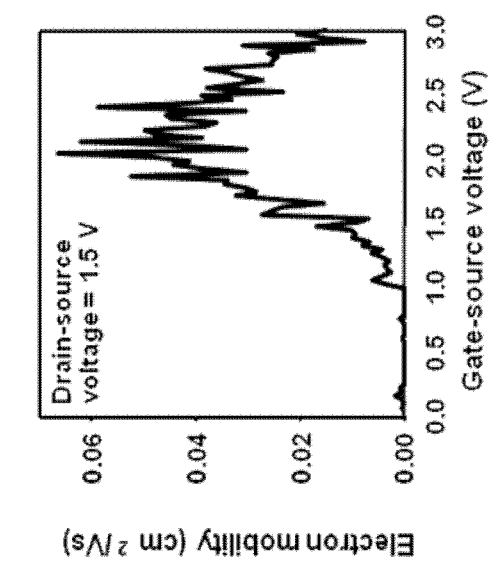
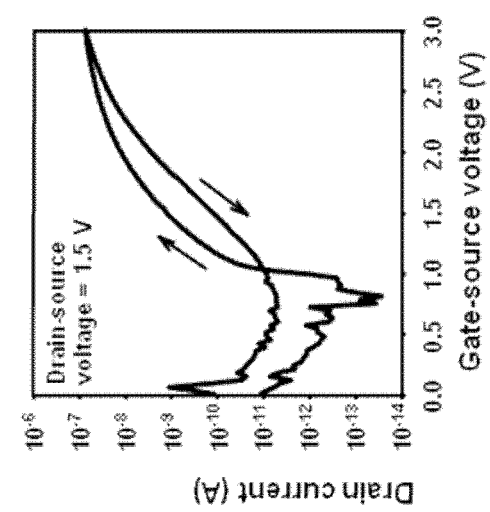
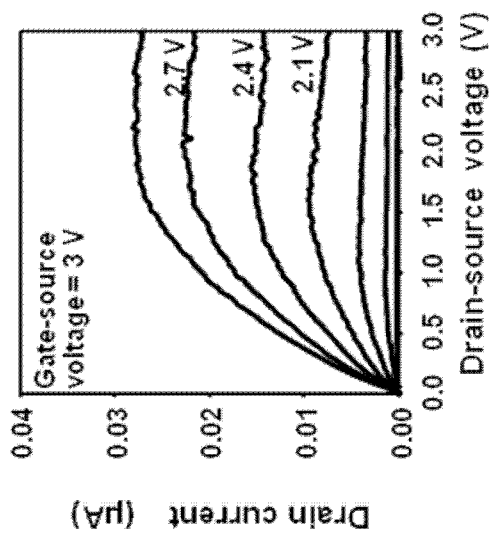

THIOCYANATO OR ISOTHIOCYANATO SUBSTITUTED NAPHTHALENE DIIMIDE AND RYLENE DIIMIDE COMPOUNDS AND THEIR USE AS N-TYPE SEMICONDUCTORS

BACKGROUND

Recent developments in organic-based light-emitting diodes (OLEDs), photovoltaics (OPVs), and field-effect transistors (OFETs) have opened up many opportunities in the field of organic electronics. One of the challenges in this field is to develop thin film devices that have environmentally stable electron-transporting (n-type) organic semiconductors with high mobility. The performance and stability of organic n-type materials have significantly lagged behind their p-type counterparts. Some challenges for advancing the technology of organic n-type materials include their vulnerability to ambient conditions (e.g., air) and solution-processability. For example, it is desirable for these materials to be soluble in common solvents so that they can be formulated into inks for inexpensive printing processes.

The most common air-stable n-type organic semiconductors include perfluorinated copper phthalocyanine ($CuF_{16}Pc$), fluoroacyl oligothiophenes (e.g., DFCO-4TCO), N,N'-fluorocarbon-substituted naphthalene diimides (e.g., NDI-F, NDI-XF), cyano-substituted perylene diimides (e.g., $PDI-FCN_2$), and cyano-substituted naphthalene diimides (e.g., $NDI-8CN_2$). See, e.g., Bao et al. (1998), *J. Am. Chem. Soc.*, 120: 207-208; de Oteyza et al. (2005), *Appl. Phys. Lett.*, 87: 183504; Schon et al. (2000), *Adv Mater.* 12: 1539-1542; Ye et al. (2005), *Appl. Phys. Lett.*, 86: 253505; Yoon et al. (2006), *J. Am. Chem. Soc.*, 128: 12851-12869; Tong et al. (2006), *J. Phys. Chem. B.*, 110: 17406-17413; Yuan et al. (2004), *Thin Solid Films*, 450: 316-319; Yoon et al. (2005), *J. Am. Chem. Soc.*, 127: 1348-1349; Katz et al. (2000), *J. Am. Chem. Soc.*, 122: 7787-7792; Katz et al. (2000), *Nature (London)*, 404: 478-481; Katz et al (2001), *Chem. Phys. Chem.*, 3: 167-172; Jung et al. (2006), *Appl. Phys. Lett.*, 88: 183102; Yoo et al. (2006), *IEEE Electron Device Lett.*, 27: 737-739; Jones et al. (2004), *Angew. Chem., Int. Ed. Engl.*, 43: 6363-6366; and Jones et al. (2007), *J. Am. Chem. Soc.*, 129: 15259-15278. Rylene imides are particularly attractive because of their robust nature, flexible molecular orbital energetics, and excellent charge transport properties. However, high-mobility rylene compounds, including $PDI-FCN_2$ and NDI-F, have poor solubility. Soluble rylene compounds, on the other hand, usually have poor charge transport properties.

Accordingly, given potential applications in inexpensive and large-area organic electronics that can be produced by high-throughput reel-to-reel manufacture, the art desires new organic n-type semiconducting compounds, especially those possessing desirable properties such as air stability, high charge transport efficiency, and good solubility in common solvents.

SUMMARY

In light of the foregoing, it is an object of the present invention to provide compounds that can be utilized as organic semiconductors and related materials, compositions, composites, and/or devices that can address various deficiencies and shortcomings of the state-of-the-art, including those outlined above.

More specifically, the present invention provides thiocyanato substituted naphthalene diimide and rylene diimede compounds and derivatives which have semiconducting activity. Materials prepared from these compounds have demonstrated unexpected properties and results. For example, it has been discovered that, when compared to related representative compounds, compounds of the present invention can have higher carrier mobility and/or better current modulation characteristics in field-effect devices (e.g., thin-film transistors). In addition, it has been discovered that compounds of the present invention can possess certain processing advantages compared to related representative compounds such as better solubility to permit solution-processability and/or good stability at ambient conditions, for example, air stability. Further, the compounds can be embedded with other components for utilization in a variety of semiconductor-based devices.

The problem is solved by compounds of formula I:

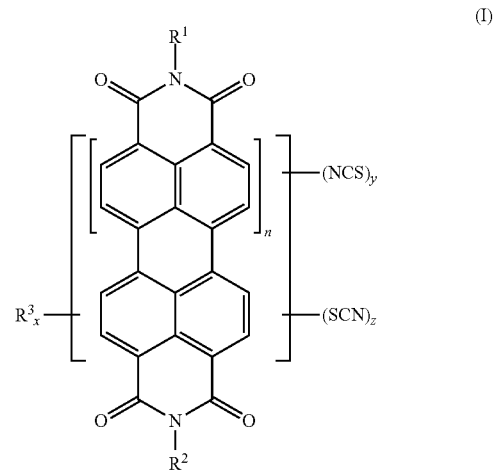

(I)

wherein:

$R^1$ and $R^2$, at each occurrence, independently are selected from H, a $C_{1-30}$ alkyl group, a $C_{2-30}$ alkenyl group, a $C_{2-30}$ alkynyl group, a $C_{1-30}$ haloalkyl group, and a 3-22 membered cyclic moiety, each optionally substituted with 1-4 groups independently selected from halogen, —CN, —$NO_2$, —C(O)H, —C(O)OH, —$CONH_2$, —OH, —$NH_2$, —CO($C_{1-10}$ alkyl), —C(O)O$C_{1-14}$ alkyl, —CONH($C_{1-14}$ alkyl), —CON($C_{1-14}$ alkyl)$_2$, —S—$C_{1-14}$ alkyl, —O—$(CH_2CH_2O)_n(C_{1-14}$ alkyl), —NH($C_{1-14}$ alkyl), —N($C_{1-14}$ alkyl)$_2$, a $C_{1-14}$ alkyl group, a $C_{2-14}$ alkenyl group, a $C_{2-14}$ alkynyl group, a $C_{1-14}$ haloalkyl group, a $C_{1-14}$ alkoxy group, a $C_{6-14}$ aryl group, a $C_{3-14}$ cycloalkyl group, a 3-14 membered cycloheteroalkyl group, and a 5-14 membered heteroaryl group; $R^3$ independently are selected from halogen-, CN, —$NO_2$, —C(O)O($C_{1-14}$alkyl), —C(O)O($C_{6-14}$ aryl), —CHO, $C_{1-14}$ alkylsulfon, $C_{6-14}$ arylsulfon, a sulfonic acid $C_{1-14}$ alkylester or $C_{6-14}$ arylester group, —$CONH_2$, —CONH($C_{1-14}$alkyl), —CONH($C_{6-14}$ aryl), —CON($C_{1-14}$alky)$_2$, —CON($C_{1-14}$ alkyl)($C_{6-14}$ aryl), —CON($C_{6-14}$ aryl)$_2$, —C(O)H, a $C_{1-14}$ alkoxy group, a $C_{1-14}$ alkylthio group, a $C_{6-14}$aryloxy group, a $C_{6-14}$arylthio group, a $C_{1-14}$ alkyl group, a 3-14 membered cycloheteroalkyl group, a $C_{6-20}$ aryl group and a 5-20 membered heteroaryl group; and n is 0, 1, 2, or 3;

x is 0, 1, 2, 3 or 4 if n is >0;

y is 1, 2, 3 or 4 if z is 0, and 0, 1, 2, 3 or 4 if z is >0;

z is 1, 2, 3 or 4 if y is 0, and 0, 1, 2, 3 or 4 if y is >0.

The present invention also provide methods of preparing such compounds and semiconductor materials, as well as various compositions, composites, and devices that incorporate the compounds and semiconductor materials disclosed herein.

The foregoing as well as other features and advantages of the present invention will be more fully understood from the following figures, description, and claims.

DETAILED DESCRIPTION

Figure 1:
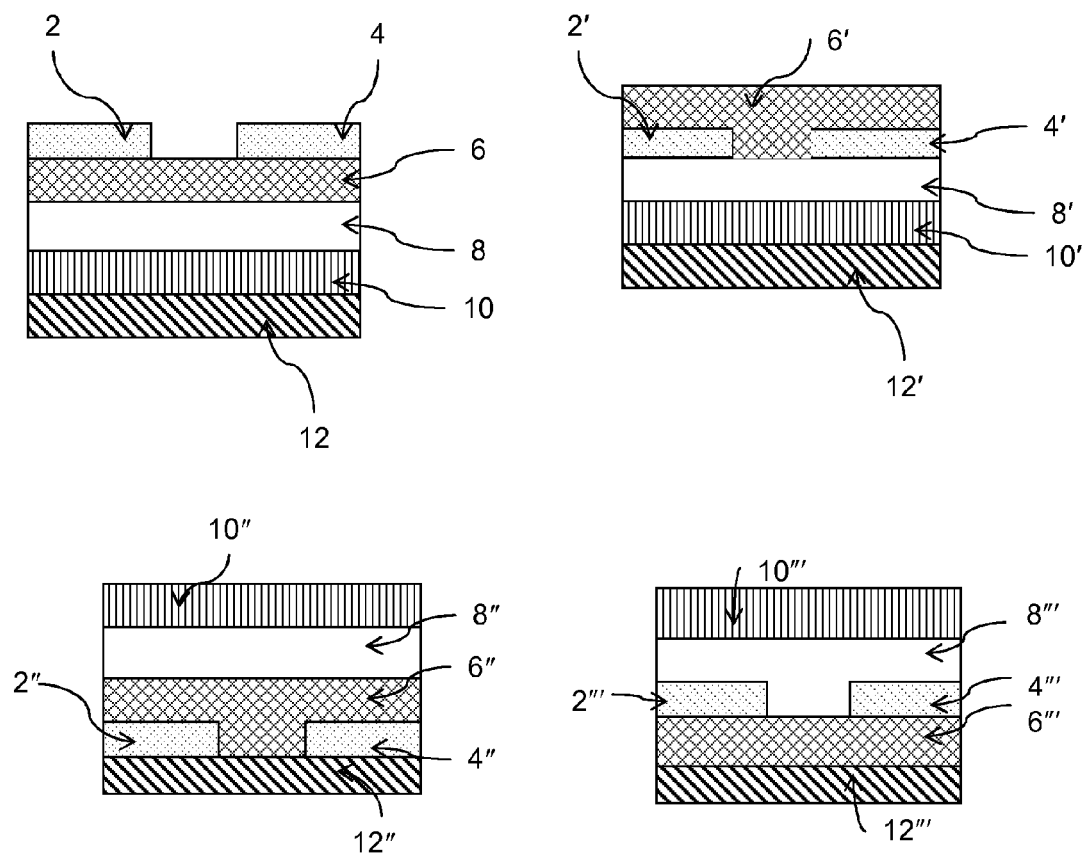
FIG. 1 illustrates different configurations of field effect transistors.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present invention, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise.

As used herein, "halo" or "halogen" refers to fluoro, chloro, bromo, and iodo.

As used herein, "alkoxy" refers to —O-alkyl group. Examples of alkoxy groups include, but are not limited to, methoxy, ethoxy, propoxy (e.g., n-propoxy and isopropoxy), t-butoxy groups, and the like. The alkyl group in the —O-alkyl group can be substituted as described herein.

As used herein, "alkylthio" refers to an —S-alkyl group. Examples of alkylthio groups include, but are not limited to, methylthio, ethylthio, propylthio (e.g., n-propylthio and iso-propylthio), t-butylthio groups, and the like. The alkyl group in the —S-alkyl group can be substituted as described herein.

As used herein, "oxo" refers to a double-bonded oxygen (i.e., =O).

$R^1$, $R^2$ can be a $C_{1-30}$ alkyl group. As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl), and the like. An alkyl group can have 1 to 30 carbon atoms, for example 1 to 20 carbon atoms (i.e., $C_{1-20}$ alkyl group). A lower alkyl group typically has up to 4 carbon atoms. Examples of lower alkyl groups include methyl, ethyl, propyl (e.g., n-propyl and isopropyl), and butyl groups (e.g., n-butyl, isobutyl, s-butyl, t-butyl). In some embodiments, alkyl groups can be substituted as disclosed herein.

$R^1$, $R^2$ can be a $C_{1-30}$ haloalkyl group. As used herein, "haloalkyl" refers to an alkyl group having one or more halogen substituents. A haloalkyl group can have 1 to 30 carbon atoms, for example 1 to 10 carbon atoms (i.e., $C_{1-10}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-20}$ haloalkyl group can have the formula —$C_aH_{2a+1-b}X_b$, wherein X, at each occurrence, is F, Cl, Br, or I, a is an integer in the range of 1 to 20, and b is an integer in the range of 1 to 41, provided that b is not greater than 2a+1.

$R^1$, $R^2$ can be a $C_{2-30}$ alkenyl group. As used herein, "alkenyl" refers to a straight-chain or branched alkyl group having one or more carbon-carbon double bonds. In various embodiments, an alkenyl group can have 2 to 30 carbon atoms, for example, 2 to 10 carbon atoms (i.e., $C_{2-10}$ alkenyl group). Examples of alkenyl groups include, but are not limited to, ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In some embodiments, alkenyl groups can be substituted as disclosed herein.

$R^1$, $R^2$ can be a $C_{2-30}$ alkynyl group. As used herein, "alkynyl" refers to a straight-chain or branched alkyl group having one or more triple carbon-carbon bonds. Examples of alkynyl groups include ethynyl, propynyl, butynyl, pentynyl, and the like. The one or more triple carbon-carbon bonds can be internal (such as in 2-butyne) or terminal (such as in 1-butyne). In various embodiments, an alkynyl group can have 2 to 30 carbon atoms, for example, 2 to 10 carbon atoms (i.e., $C_{2-10}$ alkynyl group). In some embodiments, alkynyl groups can be substituted as disclosed herein.

$R^1$, $R^2$ can be a 3-22 membered cyclic moiety. As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-22 ring atoms, and can be optionally substituted as described herein. In some embodiments where the cyclic moiety is a monocyclic moiety, the monocyclic moiety can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In some embodiments where the cyclic moiety is a polycyclic moiety, the polycyclic moiety can include two or more rings fused to each other or connected to each other via a single bond or a spiro atom, or one or more bridged atoms. A polycyclic moiety can include an 8-22 membered aromatic or non-aromatic, carbocyclic or heterocyclic ring, such as a $C_{8-22}$ aryl group or an 8-22 membered heteroaryl group, each of which can be optionally substituted as described herein.

$R^1$, $R^2$ can be a cycloalkyl group having 3 to 22 carbon atoms. As used herein, "cycloalkyl" refers to a non-aromatic carbocyclic group including cyclized alkyl, alkenyl, and alkynyl groups. The cycloalkyl group can have 3 to 22 carbon atoms, for example, 3 to 14 carbon atoms (i.e., $C_{3-14}$ cycloalkyl group). The cycloalkyl group can be monocyclic (e.g., cyclohexyl) or polycyclic (e.g., containing fused, bridged, and/or spiro ring systems), wherein the carbon atoms are located inside or outside of the ring system. Examples of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as disclosed herein.

As used herein, "heteroatom" refers to an atom of any element other than carbon or hydrogen and includes, for example, nitrogen, oxygen, silicon, sulfur, phosphorus, and selenium.

$R^1$, $R^2$ can be a cycloheteroalkyl group having 3 to 22 ring atoms. As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 22 ring atoms, for example, 3 to 14 ring atoms (i.e., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as disclosed herein.

$R^1$, $R^2$ can be an aryl group having from 6 to 22 ring atoms. As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have from 6 to 22 ring atoms in its ring system, for example, 6 to 14 ring atoms (i.e., $C_{6-14}$ aryl group), which can include multiple fused rings. In some embodiments, a polycyclic aryl group can have from 8 to 22 carbon atoms. Any suitable ring position of the aryl group can be covalently linked to the defined chemical structure. Examples of aryl groups having only aromatic carbocyclic ring(s) include, but are not limited to, phenyl, 1-naphthyl (bicyclic), 2-naphthyl (bicyclic), anthracenyl (tricyclic), phenanthrenyl (tricyclic) and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include, but are not limited to, benzodioxanyl, benzodioxolyl, chromanyl, indolinyl groups, and the like. In some embodiments, aryl groups can be substituted as disclosed herein. In some embodiments, an aryl group can have one or more halogen substituents and can be referred to as a "haloaryl" group.

Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

$R^1$, $R^2$ can be a heteroaryl group having 5 to 22 ring atoms. As used herein, "heteroaryl" refers to an aromatic monocyclic ring system containing at least one ring heteroatom selected from O, N, S, Si, and Se or a polycyclic ring system where at least one of the rings present in the ring system is aromatic and contains at least one ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have from 5 to 22 ring atoms (e.g., 5-14 membered heteroaryl group) and contain 1-5 ring heteroatoms. The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

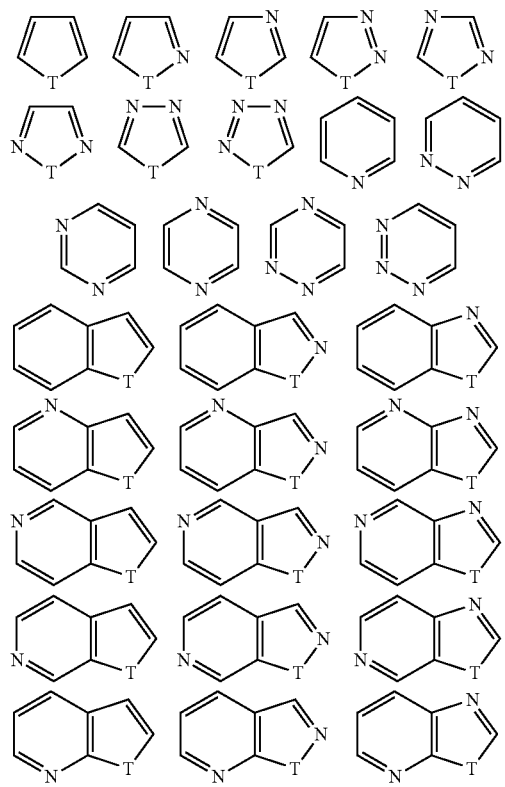

where T is O, S, NH, N-alkyl, N-aryl, N-(arylalkyl) (e.g., N-benzyl), $SiH_2$, SiH-(alkyl), Si(alkyl)$_2$, SiH-(arylalkyl), Si-(arylalkyl)$_2$, or Si(alkyl)(arylalkyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted as disclosed herein.

Compounds of the present invention can include a "divalent group" defined herein as a linking group capable of forming a covalent bond with two other moieties. For example, compounds of the present invention can include a divalent $C_{1-20}$ alkyl group, such as, for example, a methylene group.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present invention include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt or ester formation, kinetic resolution, enzymatic resolution, and asymmetric synthesis. The present invention also encompass cis and trans isomers of compounds containing alkenyl moieties (e.g., alkenes and imines). It is also understood that the present invention encompass all possible regioisomers in pure form and mixtures thereof, which can be obtained with standard separation procedures known to those skilled in the art, for examples, column chromatography, thin-layer chromatography, simulated moving-bed chromatography, and high-performance liquid chromatography. For example, perylene compounds of the present invention include perylene derivatives in their pure form or mixtures thereof, where the perylene derivatives can be substituted with 1, 2, 3, 4, 5, 6, 7, or 8 substituents. Naphthalene compounds of the present invention include naphthalene derivatives in their pure form or mixtures thereof, where the naphthalene derivatives can be substituted with 1, 2, 3 or 4 substituents. Specifically, the perylene derivatives can include compounds having the moiety:

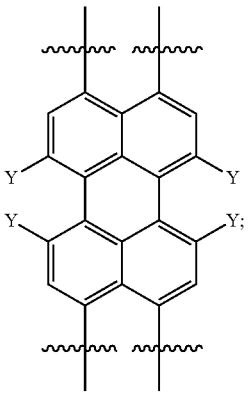

where Y, at each occurrence, can be H, a thiocyanato or an isothiocyanato group.

In various embodiments, two of the Y groups are H and the other two Y groups independently are a thiocyanato or an isothiocyanato group. Accordingly, in the embodiments where two of the Y groups are H and the other two independently area thiocyanato or an isothiocyanato group, compounds of the present invention can have regioisomers having the formulae:

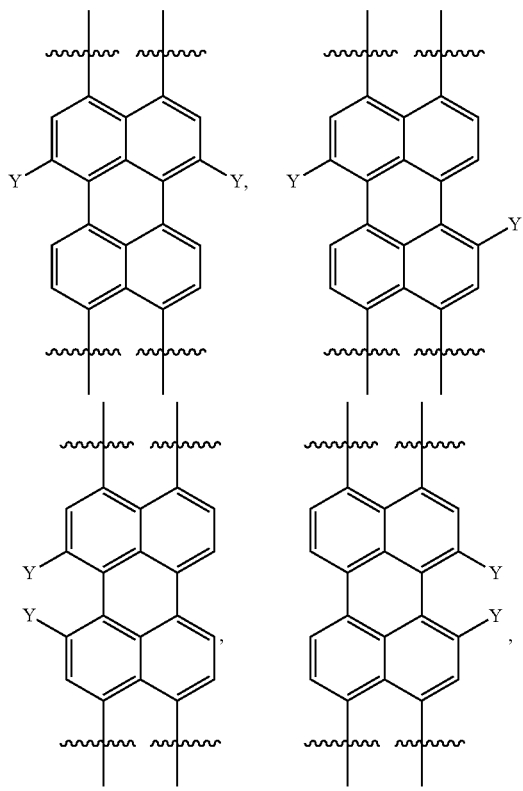

-continued

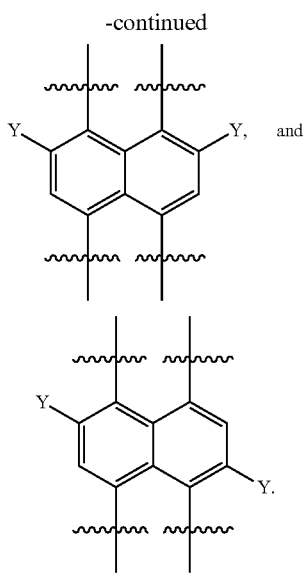

In certain embodiments, compounds of the present invention can include compounds having formula i or ii:

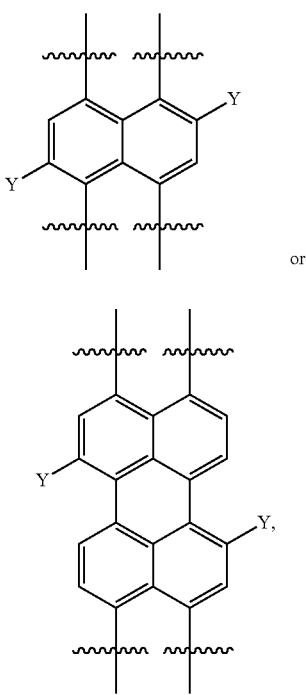

i or ii or mixtures thereof, where Y independently is a thiocyanato group or an isothiocyanato group.

As used herein, a "p-type semiconducting material" or a "p-type semiconductor" refers to a semiconducting material having holes as the majority current carriers. In some embodiments, when a p-type semiconducting material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, a "n-type semiconducting material" or a "n-type semiconductor" refers to a semiconducting material having electrons as the majority current carriers. In some embodiments, when a n-type semiconducting material is deposited on a substrate, it can provide an electron mobility in excess of about $10^{-5}$ cm$^2$/Vs. In the case of field-effect devices, an n-type semiconductor can also exhibit a current on/off ratio of greater than about 10.

As used herein, "field effect mobility" refers to a measure of the velocity with which charge carriers, for example, holes (or units of positive charge) in the case of a p-type semiconducting material and electrons in the case of an n-type semiconducting material, move through the material under the influence of an electric field.

As used herein, a compound can be considered "ambient stable" or "stable at ambient conditions" when the carrier mobility or the reduction-potential of the compound is maintained at about its initial measurement when the compound is exposed to ambient conditions, for example, air, ambient temperature, and humidity over a period of time. For example, a compound can be described as ambient stable if its carrier mobility or reduction potential does not vary more than 20% or more than 10% from its initial value after exposure to ambient conditions, i.e., air, humidity and temperature, over a 3 day, 5 day, or 10 day period.

As used herein, "solution-processable" refers to compounds, materials, or compositions that can be used in various solution-phase processes including spin-coating, printing (e.g., inkjet printing, screen printing, pad printing, gravure printing, flexographic printing, offset printing, microcontact printing, and lithographic printing), spraying, electrospray coating, drop casting, zone-casting, dip coating, and blade coating.

At various places in the present application temperatures are disclosed in ranges. It is specifically intended that the description includes narrower ranges of temperatures within such ranges, as well as the maximum and minimum temperatures embracing such range of temperatures.

Throughout the specification, structures may or may not be presented with chemical names. Where any question arises as to nomenclature, the structure prevails.

In one aspect, the present invention provide compounds having formula Ia, Ib or Ic:

Ia

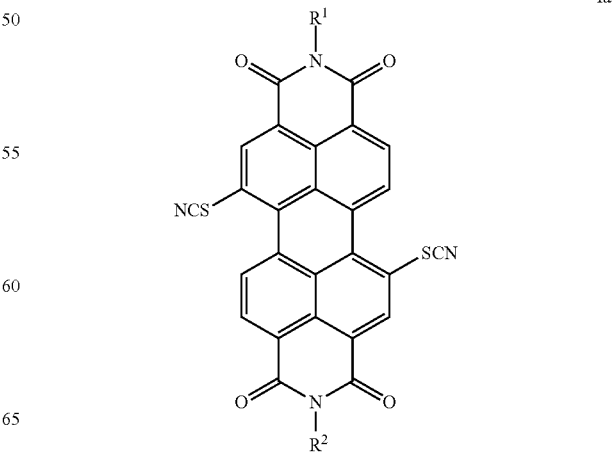

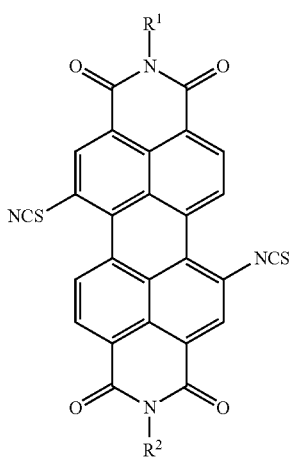

Ib

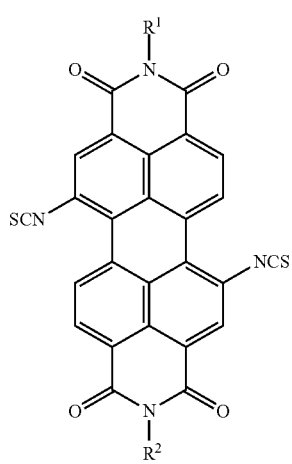

Ic

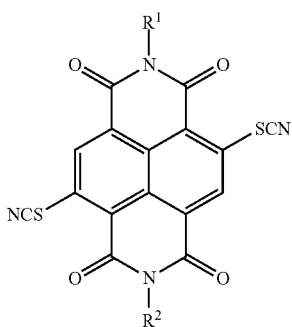

wherein: R¹ and R² are as defined above.

In a further aspect, the present invention provides compounds having formula Id, Ie, or If:

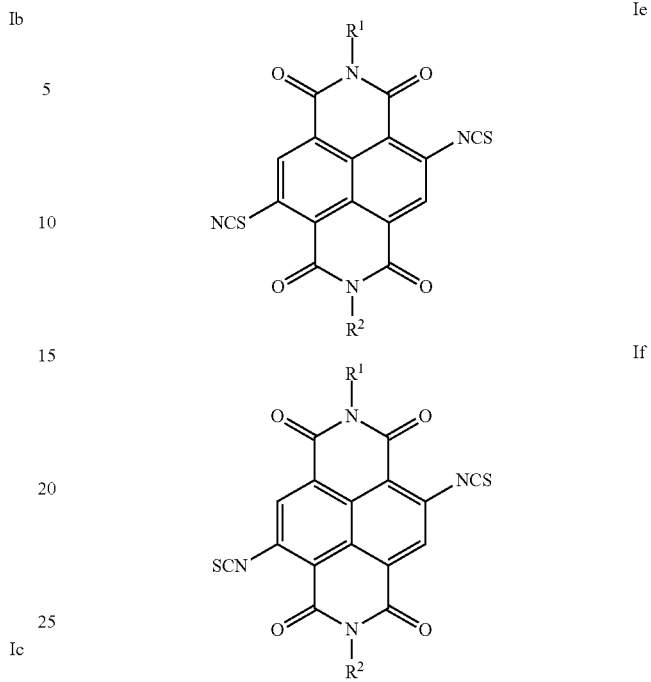

wherein R¹, R² are as defined above.

R¹ and R², at each occurrence, are independently selected from H, a $C_{1-30}$ alkyl group, a $C_{2-30}$ alkenyl group, a $C_{2-30}$ alkynyl group, a $C_{1-30}$ haloalkyl group, and a 3-22 membered cyclic moiety, each optionally substituted with 1-4 groups independently selected from halogen, —CN, —NO$_2$, —C(O)H, —C(O)OH, —CONH$_2$, —OH, —NH$_2$, —CO($C_{1-14}$ alkyl), —C(O)CO$_{1-14}$ alkyl, —CONH($C_{1-14}$ alkyl), —CON($C_{1-14}$ alkyl)$_2$, —S—$C_{1-14}$ alkyl, —O—(CH$_2$CH$_2$O)$_n$($C_{1-14}$ alkyl), —NH($C_{1-14}$ alkyl), —N($C_{1-14}$ alkyl)$_2$, a $C_{1-14}$ alkyl group, a $C_{2-14}$ alkenyl group, a $C_{2-14}$ alkynyl group, a $C_{1-14}$ haloalkyl group, a $C_{1-14}$ alkoxy group, a $C_{6-14}$ aryl group, a $C_{3-14}$ cycloalkyl group, a 3-14 membered cycloheteroalkyl group, and a 5-14 membered heteroaryl group, and n is as described herein. The 3-22 membered cyclic moiety can be selected from a $C_{6-22}$ aryl group, a 5-22 membered heteroaryl group, a $C_{3-22}$ cycloalkyl group, and a 3-22 membered cycloheteroalkyl group, each of which can be optionally substituted as described herein.

In preferred embodiments, R¹ and R², at each occurrence, are independently selected from a $C_{1-12}$ alkyl group, a $C_{1-12}$ haloalkyl group, and a 5-14 membered monocyclic moiety, each optionally substituted with 1-4 groups independently selected from halogen, —CN, —NO$_2$, —C(O)H, —C(O)OH, —CONH$_2$, —OH, —NH$_2$, —CO($C_{1-14}$ alkyl), —C(O)OC$_{1-14}$ alkyl, —CONH($C_{1-14}$ alkyl), —CON($C_{1-14}$ alkyl)$_2$, —S—$C_{1-14}$ alkyl, —O—(CH$_2$CH$_2$O)$_n$($C_{1-14}$ alkyl), —NH($C_{1-14}$ alkyl), —N($C_{1-14}$ alkyl)$_2$, a $C_{1-14}$ alkyl group, a $C_{2-14}$ alkenyl group, a $C_{2-14}$ alkynyl group, a $C_{1-14}$ haloalkyl group, a $C_{1-14}$ alkoxy group, a $C_{6-14}$ aryl group, a $C_{3-14}$ cycloalkyl group, a 3-14 membered cycloheteroalkyl group, and a 5-14 membered heteroaryl group, and n is 1, 2, or 3.

In particular embodiments, R¹ and R², at each occurrence, are independently selected from a $C_{1-12}$ alkyl group, a $C_{1-12}$ haloalkyl group, a $C_{7-20}$ arylalkyl group, and a phenyl group, wherein the phenyl group is optionally substituted with 1-4 groups independently selected from a halogen, a $C_{1-6}$ alkyl group, and a $C_{1-6}$ haloalkyl group. For example, R¹ and R², at each occurrence, are selected from —CH$_3$, —C$_2$H$_5$, —C$_3$H$_7$, —C$_4$H$_9$, —C$_5$H$_{11}$, —C$_6$H$_{13}$, —C$_8$H$_{17}$ (in particular 2-ethylhexyl), —C$_{12}$H$_{25}$, —C$_{13}$H$_{27}$, a phenyl group optionally substituted with 1-5 halo groups or C$_{1-6}$ alkyl groups, a C$_{7-12}$ phenylalkyl group wherein phenyl is optionally substituted with 1-5 halo groups in particular F atoms, or C$_{1-6}$ alkyl groups, and a C$_{1-6}$ haloalkyl group.

Examples of particular haloalkyl groups are —CF$_3$, —C$_2$F$_5$, —C$_3$F$_7$ and —CH$_2$C$_3$F$_7$.

Examples of particular arylalkyl groups are benzyl, phenylethyl and phenylpropyl.

In various embodiments, R$^3$ is an electronic-withdrawing group independently selected from halogen, —CN, —NO$_2$, —CF$_3$, —OCF$_3$, —CO$_2$(C$_{1-10}$ alkyl), —CHO, C$_1$-C$_{14}$ alkylsulfon, C$_{6-14}$ arylsulfon, a sulfonic acid —C$_{1-14}$ alkylester or —C$_{6-14}$ arylester group, —CONH(C$_{1-10}$ alkyl), —CON(C$_{1-10}$ alkyl)$_2$. For example R$^3$ can be halogen, —CN, —NO$_2$, —CF$_3$, or —OCF$_3$.

In certain embodiments, R$^3$ is F, Cl, Br, I, or —CN.

In another aspect, the present invention provides methods of preparing compounds as disclosed herein. In various embodiments, the method can include reacting a compound of formula IIa and IIb, respectively IIa

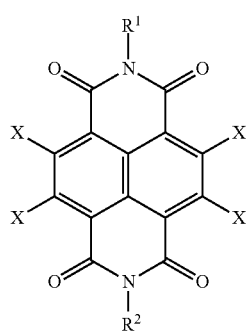

IIb

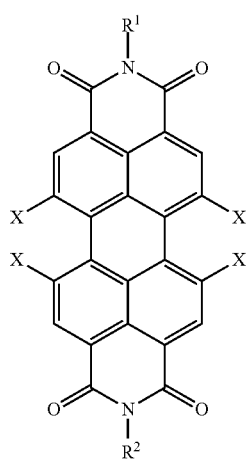

with a thiocyanate,
wherein R$^1$ and R$^2$ are as defined above, X, at each occurrence, is H or a leaving group, suitable leaving groups are F, Cl, Br, I, —OSO$_2$—C$_6$H$_4$—CH$_3$, —OSO$_2$—CH$_3$.

In various embodiments, X, at each occurrence, can be H or halogen. For example, X, at each occurrence, can be H, F, Cl, Br, or I. In certain embodiments, X, at each occurrence, can be H or Br.

In some embodiments, the thiocyanate is LiSCN, NaSCN, KSCN, NH$_4$SCN, NR$_4$SCN, PR$_4$SCN, wherein R are each independently C$_{1-18}$ alkyl, CuSCN or AgSCN. Preferably, the thiocyanate is NaSCN or KSCN.

In some embodiments, the reaction can be conducted at room temperature, for example, between 20° C. and 30° C. In some embodiments, the reaction can be conducted at a temperature that is different from room temperature. For example, the temperature can be lower or higher than room temperature. In certain embodiments, the reaction can be conducted at an elevated temperature, i.e., a temperature higher than room temperature. For example, the elevated temperature can be between 50° C. and 300° C. In particular embodiments, the elevated temperature can be between 50° C. and 180° C., for example, between 70° C. and 150° C. (e.g., 70° C. or 150° C.).

Whether the thiocyanato-compound or the isothiocyanato-compound is formed may depend on the nature of the solvent.

Solvents in which the thiocyanato-compound is predominantly or almost exclusively formed include DMSO, mixtures of DMSO with aromatic solvents such as toluene, xylene, mesitylene, tetraline, chlorobenzene, dichlorobenzene, chloronapthalene or nitrobenzene, or mixtures of DMSO with an ether such as 1,4-dioxan or tetrahydrofuran.

Solvents in which the isothiocyanato-compound is predominantly or almost exclusively formed include methyl ethyl ketone and isobutyl methyl ketone. Reaction in the presence of a phase transfer catalyst such as a quaternary ammonia salt favors the formation of the isothiocyanato compound.

In any case, where mixtures of thiocyanato-, isothiocyanato- and mixed thiocyanatoisothiocyanato-compounds are formed, the pure compounds can be isolated by standard methods, such as chromatography.

In various embodiments, a compound of formula IIa and IIb, respectively, can be prepared by reacting a compound of formula IIIa and IIIb, respectively IIIa

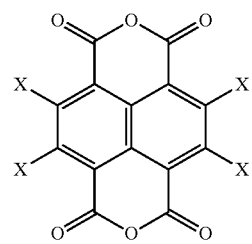

IIIb

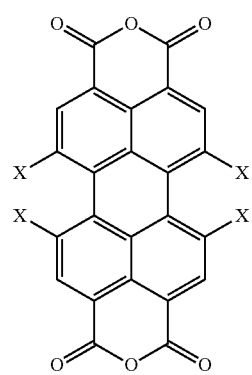

with an primary amine R$^1$—NH$_2$ or R$^2$—NH$_2$ in an aprotic solvent, wherein X, R$^1$ and R$^2$ are as defined herein. This is preferred for the preparation of compounds IIb.

However, in case of the preparation of compounds IIa, it is more preferred to chlorineate or brominate a naphthalene diimide compound of formula Va.

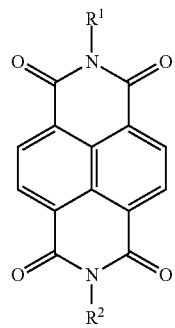

Va using a chlorination and a bromination agent respectively.

This may result in higher yields of compounds IIa, as compared to the bromination of naphthalenetetracarboxylic acid dianhydride IVa and the subsequent imidation of compounds IIIa with $R^1$—$NH_2$ and/or $R^2$—$NH_2$.

The present invention also concerns a process for producing a bromo-substituted naphthalene diimide compound of formula IIa

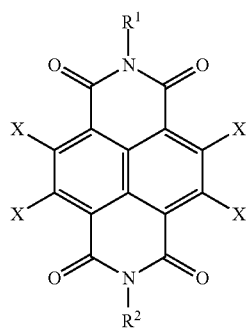

IIa wherein X are independently H, Cl or Br with the proviso that at least one X is Cl or Br, $R^1$, $R^2$ are as defined in claim 1, comprising the step of chlorinating or brominating naphthalene diimide of formula Va

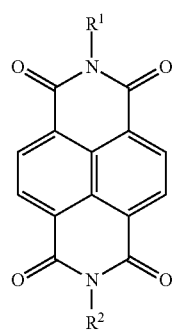

Va using a chlorination and a bromination agent, respectively.

Preferred chlorination and bromination agents are N,N'-dichloroisocyanuric acid and N,N'-dibromoisocyanuric acid, respectively.

The chlorination is preferably carried out in concentrated sulfuric acid as reaction medium (e.g. 95-98 wt.-% sulfuric acid). $FeCl_3$ and $FeBr_3$, respectively, can be added as catalysts.

The naphthalene diimide compound of formula IIa is preferably obtained by reacting naphthalenetetracarboxylic acid dianhydride with a primary amine $R^1$—$NH_2$, $R^2$—$NH_2$, or mixtures thereof, wherein $R^1$, $R^2$ are as defined herein.

In various embodiments, the aprotic solvent can include an ether. In some embodiments, the aprotic solvent can include ($C_{1-6}$ alkyl)O($CH_2CH_2O$)$_m$($C_{1-6}$ alkyl), where m can be 1, 2, 3, 4, 5, or 6. In particular embodiments, the aprotic solvent can be a solvent or a solvent mixture that includes triethylene glycol dimethyl ether. For example, the aprotic solvent can be triethylene glycol dimethyl ether.

In various embodiments, the reaction can be conducted at room temperature. In various embodiments, the reaction can be conducted at a temperature that is different from room temperature. For example, the temperature can be lower or higher than room temperature. In certain embodiments, the reaction can be conducted at an elevated temperature, i.e., a temperature higher than room temperature. For example, the elevated temperature can be between 50° C. and 300° C. In particular embodiments, the elevated temperature can be between 50° C. and 200° C., for example, between 70° C. and 180° C. (e.g., 165° C.).

Compounds of formula IIIa and IIIb, respectively, can be prepared by bromination of compounds of formula IVa and IVb, respectively,

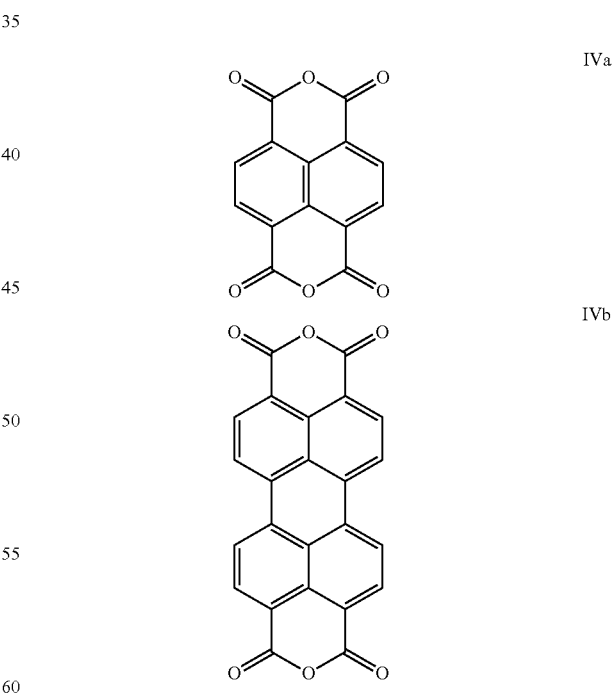

using known bromination agents such as bromine, N,N'-dibromoisocyanuric acid or Nbromosuccinimide.

Bromination of compound IVb is described in DE 195 47 209 and in F. Würthner, Chem. Commun. 2004, 1564-1579. The bromination of perylene diimdes is described in J. Org. Chem. 2007, 72, 5973-5979.

Compounds of the present invention can be prepared in accordance with the procedures outlined in Scheme 1 below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatograpy (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Scheme 1

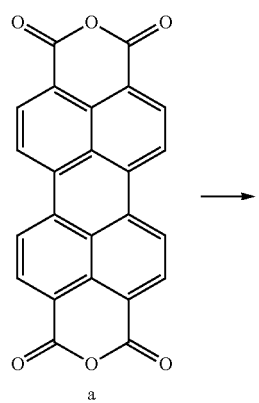

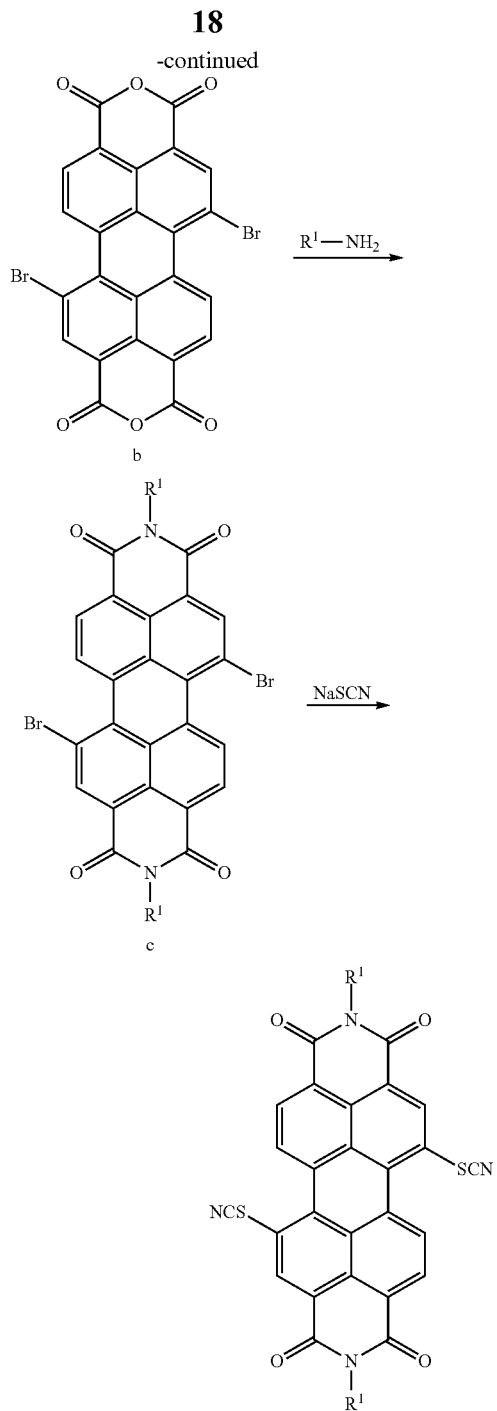

As shown in Scheme 1, perylene-3,4:9,10-tetracarboxylic acid dianhydride (PDA), a, can be brominated at 1,7-positions to provide PDA-Br$_2$, b, which upon reacting with a primary amine can provide a bis(dicarboximide), c. The substitution of the bromo groups in c by thiocyanato groups can produce a dithiocyanato-substituted bis(dicarboximide), d. Although not shown in Scheme 1, the bromination of a can also produce regioisomers of b, for example, 1,6-dibromo-perylene-3,4:9,10-tetracarboxylic acid dianhydride, subsequently resulting in regioisomers of d, for example, 1,6-dithiocyanato bis(dicarboximide). Instead of PDA, the bis(dicarboximide) resulting from the amination of a can be likewise brominated to give compound c.

In an analogous way, naphthalenedithiocyanato bis(dicarboximide) can be prepared from naphthalene-3,4:7,8-tetracarboxylic acid dianhydride according to Scheme 2:

Scheme 2

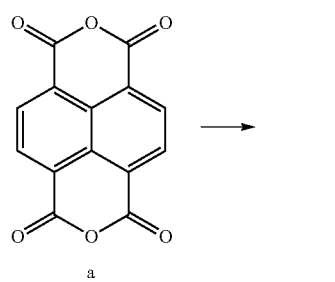
a

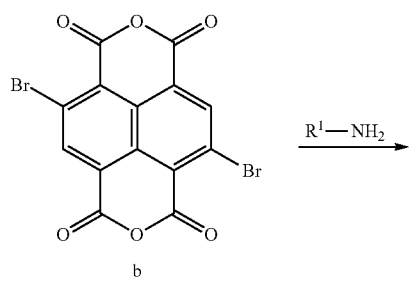
b

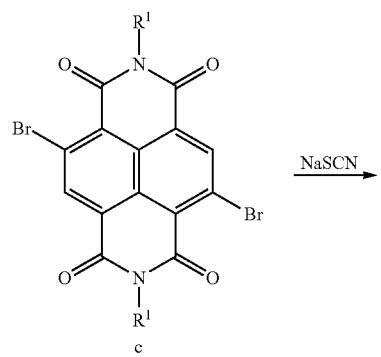
c

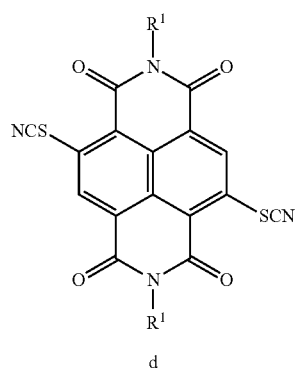
d

However, it is preferred to prepare the naphthalenedithiocyanato bis(dicarboximide) compounds following Scheme 3:

Scheme 3

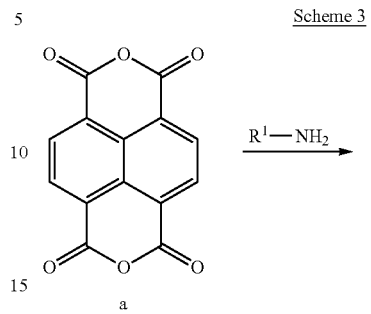
a

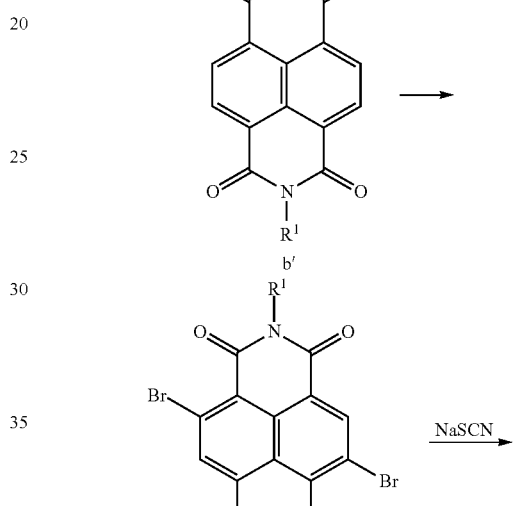
b′ c′

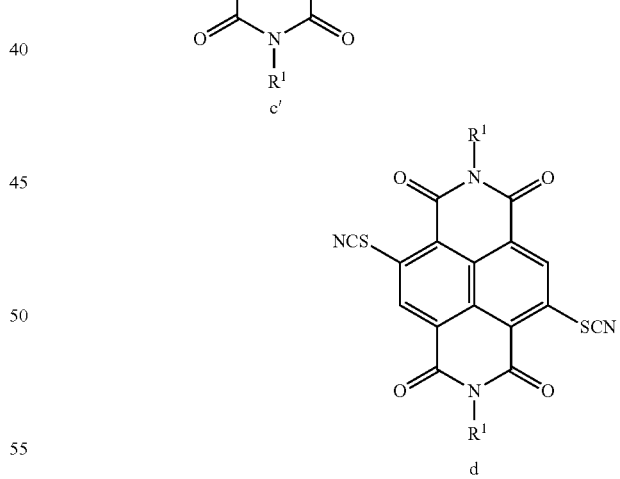
d

Compounds of formula I can be used to prepare semiconductor materials (e.g., compositions and composites), which in turn can be used to fabricate various articles of manufacture, structures, and devices. Semiconductor materials incorporating one or more compounds of the present invention can exhibit n-type semiconducting activity.

As the compounds disclosed herein are soluble in common solvents, the present invention can offer processing advantages in fabricating electrical devices such as thin film semiconductors, field-effect devices, organic light emitting diodes (OLEDs), organic photovoltaics, photodetectors, capacitors, and sensors. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. Examples of common inorganic solvents include water and ionic liquids.

Accordingly, the present invention further provides compositions that include one or more compounds disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, such compositions can include one or more compounds disclosed herein, for example, two or more different compounds of the present invention can be dissolved in an organic solvent to prepare a composition for deposition. In certain embodiments, the composition can include two or more regioisomers. Further, it should be understood that the devices described herein also can comprise one or more compounds of the present invention, for example, two or more regioisomers as described herein.

Various deposition techniques, including various solution-processing techniques, have been used in preparing organic electronics. For example, much of the printed electronics technology has focused on inkjet printing, primarily because this technique offers greater control over feature position and multilayer registration. Inkjet printing is a non-contact process, which offers the benefits of not requiring a preformed master (compared to contact printing techniques), as well as digital control of ink ejection, thereby providing drop-on-demand printing. Micro dispensing is another non-contact method of printing. However, contact printing techniques have the key advantage of being wellsuited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes a noncontact process, for example, injet printing, micro dispensing, and the like, and a contact process, for example, screen-printing, gravure printing, offset printing, flexographic printing, lithographic printing, pad printing, microcontact printing, and the like. Other solution processing techniques include, for example, spin coating, drop-casting, zone casting, dip coating, blade coating, or spraying. In addition, the deposition step can be carried out by vacuum vapor-deposition.

The present invention, therefore, further provide methods of preparing a semiconductor material. The methods can include preparing a composition that includes one or more compounds disclosed herein dissolved or dispersed in a liquid medium such as a solvent or a mixture of solvents, and depositing the composition on a substrate to provide a semiconductor material (e.g., a thin film semiconductor) that includes one or more compounds disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatiblizing agents, curing agents, initiators, humectants, antifoaming agents, wetting agents, pH modifiers, biocides, and bactereriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the compounds and the semiconductor materials disclosed herein also as well as methods of making the same are within the scope of the present invention. Accordingly, the present invention provides articles of manufacture such as the various devices described herein that include a composite having a semiconductor material of the present invention, a substrate component, and/or a dielectric component. The substrate component can be selected from materials including doped silicon, an indium tin oxide (ITO), ITO-coated glass, ITO-coated polyimide or other plastics, aluminum or other metals alone or coated on a polymer or other substrate, a doped polythiophene or other polymers, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., described in Yoon, M-H. et al., *PNAS*, 102 (13): 4678-4682 (2005), the entire disclosure of which is incorporated by reference herein), and hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene)poly(styrenesulfonate) (PEDOT:PSS), polyaniline (PANI), polypyrrole (PPy)). One or more of the composites described herein can be incorporated within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

An aspect of the present invention, therefore, relates to methods of fabricating an organic field effect transistor that incorporates a semiconductor material of the present invention. The semiconductor materials of the present invention can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIG. 1 illustrates the four common types of OFET structures: top-contact bottom-gate structure (top left), bottom-contact bottom-gate structure (top right), bottom-contact top-gate structure (bottom left), and top-contact top-gate structure (bottom right). As shown in FIG. 1, an OFET can include a dielectric layer (e.g., shown as 8, 8', 8", and 8"'), a semiconductor layer (e.g., shown as 6, 6', 6", and 6"'), a gate contact (e.g., shown as 10, 10', 10", and 10"'), a substrate (e.g., shown as 12, 12', 12", and 12"'), and source and drain contacts (e.g., shown as 2, 2', 2", 2"', 4, 4', 4", and 4"').

In certain embodiments, OTFT devices can be fabricated with the present compounds on doped silicon substrates, using $SiO_2$ as the dielectric, in top-contact geometries. In particular embodiments, the active semiconducting layer which incorporates at least a compound of the present invention can be deposited by vacuum vapor deposition at room temperature or at an elevated temperature. In other embodiments, the active semiconducting layer which incorporates at least a compound of the present invention can be applied by solution-based process, for example, spin-coating or jet printing. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a compound of the present invention can be deposited at room temperature or at an elevated temperature. In other embodiments, the active semiconducting layer which incorporates at least a compound of the present invention can be applied by spin-coating or printing as described herein. Gate and source/drain contacts can be made of Au, other metals, or conducting polymers and deposited by vapor-deposition and/or printing.

Other articles of manufacture in which compounds of the present invention are useful are photovoltaics or solar cells. Compounds of the present invention can exhibit broad optical absorption and/or a very positively shifted reduction potential making them desirable for such applications. Accordingly, the compounds described herein can be used as an n-type semiconductor in a photovoltaic design, which includes an adjacent p-type semiconducting material that forms a p-n junction. The compounds can be in the form of a thin film semiconductor, which can be a composite of the thin film semiconductor deposited on a substrate. Exploitation of compounds of the present invention in such devices is within the knowledge of the skilled artisan.

Accordingly, another aspect of the present invention relates to methods of fabricating an organic light-emitting transistor, an organic light-emitting diode (OLED), or an organic photovoltaic device that incorporates one or more semiconductor materials of the present invention.

The following examples are provided to illustrate further and to facilitate understanding of the present invention and are not in any way intended to limit the invention.

Unless otherwise noted, all reagents were purchased from commercial sources and used without further purification. Some reagents were synthesized according to known procedures. Anhydrous tetrahydrofuran (THF) was distilled from sodium/benzophenone. Reactions were carried out under nitrogen unless otherwise noted. UV-Vis spectra were recorded on a Cary Model 1 UV-vis spectrophotometer. NMR spectra were recorded on a Varian Unity Plus 500 spectrometer and a 400 MHz spectrometer ($^1$H, 400 MHz and 500 MHz; $^{13}$C, 125 MHz). Electrospray mass spectrometry was performed on a Thermo Finnegan model LCQ Advantage mass spectrometer.

EXAMPLES

FIG. 1 shows the four common types of OFET structures: top-contact bottom-gate structure (top left), bottom-contact bottom-gate structure (top right), bottom-contact top-gate structure (bottom left), and top-contact top-gate structure (bottom right).

FIG. 2a shows the drain current in µA versus the drain-source voltage in V at different gate-source voltages for the compound of example 1a.

FIG. 2b shows the drain current in A versus the gate-source voltage in V at a drain-source voltage of 1.5 V for the compound of example 1b.

FIG. 2c shows the electron mobility in $cm^2/Vs$ versus the gate-source voltage at a drain-source voltage of 1.5 V for the compound of example 1b.

Figure 2E:
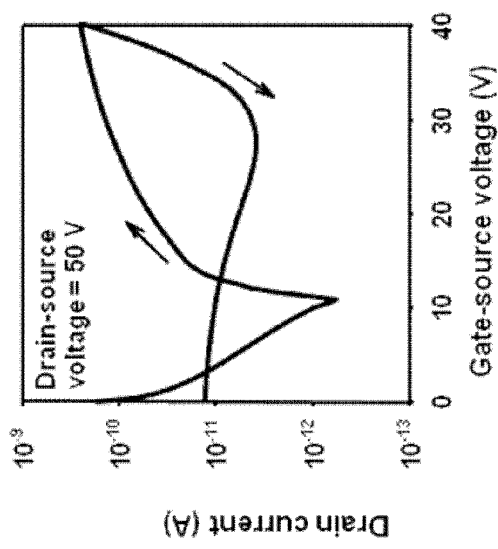
Figure 2D:
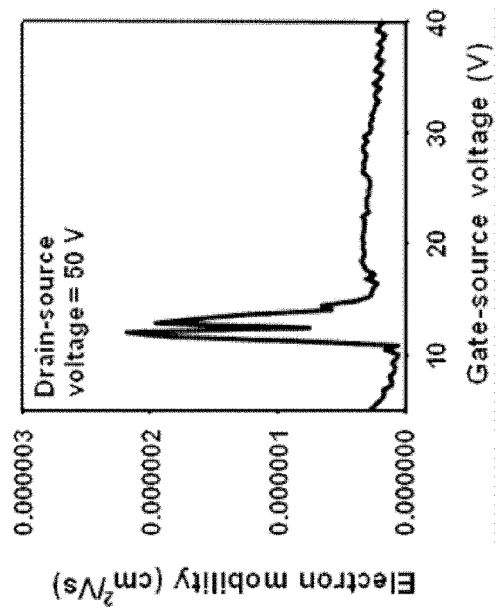

FIG. 2d shows the drain current in A versus the gate-source voltage in V at a drain-source voltage of 50 V for the compound of example 4b.

FIG. 2e shows the electron mobility in $cm^2/Vs$ versus the gate-source voltage at a drain-source voltage of 50 V for the compound of example 4b.

Figure 3A:
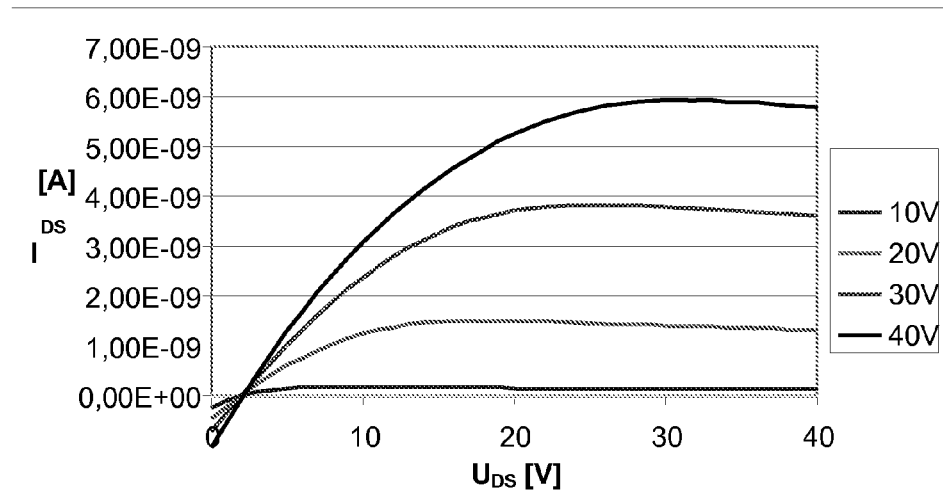

FIG. 3a shows the drain current in A versus the drain-source voltage in V at different gate-source voltages for the compound of example 3.

Figure 3B:
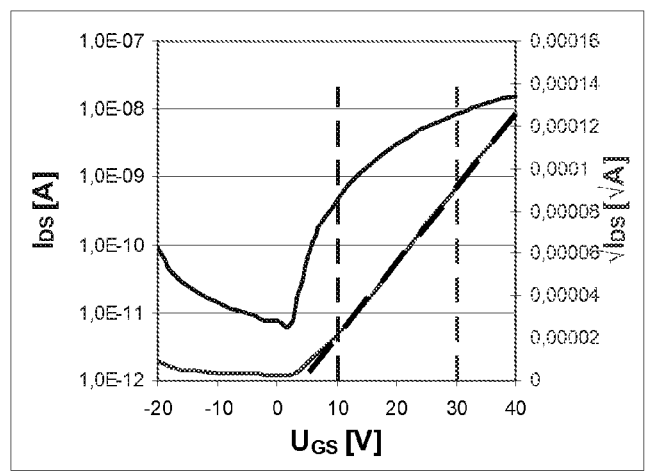

FIG. 3b shows the drain-source current in A versus the gate-source voltage in V (upper curve) and the square root of the drain-source current in $A^{1/2}$ versus the gate-source voltage in V (lower curve) for the compound of example 3.

Example 1

Example 1a

Preparation of 2,6-Dibromo-N,N'-bis(1H,1H-perfluorobutyl)-naphthalene[1,8:4,5]-bis(dicarboximide)

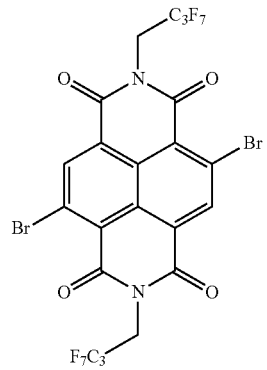

To a solution of 2.00 g (3.17 mmol) N,N'-bis(1H,1H-perfluorobutyl)naphthalene[1,8:4,5]-bis(dicarboximide) [described in H. E. Katz et al., Materials Research Society Symposium Proceedings (2002), 665 (Electronics, Optical and Optoelectronic Polymers and Oligomers), 271-280] in 240 ml of 95 to 97% strength sulfuric acid was added 1.17 g (3.96 mmol) of 97% strength N,N'-dibromoisocyanuric acid at room temperature. The reaction flask was darkened with aluminium foil. The solution was stirred for 28 hours at room temperature. Subsequently, the solution was poured on 1.5 kg ice and neutralized with NaOH. The aqueous phase was extracted twice with 750 ml dichloromethane. The combined organic extracts were dried over magnesium sulfate, filtered and concentrated to dryness. The residue was suspended in n-heptane and filtered. The filter cake obtained was dried to yield 2.29 g of a yellow solid. Recrystallization from 80 ml isobutanol yielded 2.06 g (83% of the theoretical amount) of a yellow solid showing only one spot in thin-layer chromatography.

$^1$H-NMR (400 MHz, D$_8$-THF): δ=9.00 (s, 2H), 5.08 (t, 4H) ppm.

Example 1b

Preparation of N,N'-Bis(1H,1H-perfluorobutyl)-2,6-dithiocyanato-naphthalene[1,8:4,5]-bis(dicarboximide)

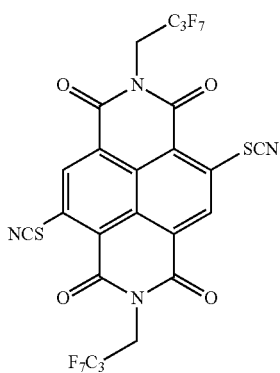

To a solution of 0.50 g (0.63 mmol) N,N'-bis(1H,1H-perfluorobutyl)-2,6-dibromonaphthalene[1,8:4,5]bis(dicarboximide) in 50 ml dimethyl sulfoxide was added within 2 hours 0.128 g (1.59 mmol) sodium thiocyanate at 95° C. while stirring continuously. The solution was stirred for another hour at 95° C. and cooled to room temperature. Then 150 ml of water were added to the reaction solution, whereby a precipitate was formed. The precipitate was filtered, washed with water and dried. The crude product was suspended in 200 ml of methylcyclohexane, heated under reflux for one hour and filtered while hot. The filter cake was washed with light petroleum and dried. This yielded 0.207 g of a yellowish brown solid which was purified by chromatography on silica gel.

$^1$H-NMR (400 MHz, CD$_2$Cl$_2$): δ=9.32 (s, 2H), 5.05 (t, 4H) ppm.

Example 2

Preparation of N,N'-Bis(1H,1H-perfluorobutyl)-2-isothiocyanato-6-thiocyanatonaphthalene[1,8:4,5]-bis(dicarboximide)

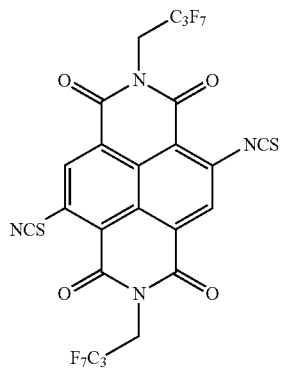

To a solution of 0.50 g (0.64 mmol) 2,6-dibromo-N,N'-bis(1H,1H-perfluorobutyl)-naphthalene[1,8:4,5]bis(dicarboximide) and 0.0056 g (0.013 mmol) Aliquat® 134 (a phase transfer catalyst) in 50 ml isobutyl methyl ketone was added within 3 hours a solution of 0.13 g (1.6 mmol) sodium thiocyanate in isobutyl methyl ketone at 95° C. The solution was stirred for another 2 hours at 95° C. and cooled to room temperature. After the addition of 3 g of silica gel the solution was concentrated to dryness. The crude product was purified by chromatography on silica gel using dichloromethane as eluent. This yielded 0.075 g (15% of the theoretical amount) of a ochre-colored solid.

$^1$H-NMR (400 MHz, CD$_2$Cl$_2$): δ=9.28 (s, 1H), 8.70 (s, 1H), 5.06 (t, 2H), 5.00 (t, 2H) ppm.

Example 3

Preparation of N,N'-Bis(phenethyl)-1,7(6)-dithiocyanatoperylene[3,4:9,10]-bis(dicarboximide)

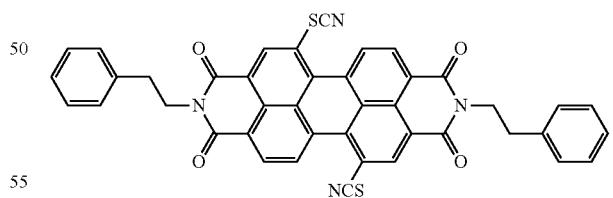

A solution of 0.50 g (0.65 mmol) 2,6-dibromo-N,N'-bis(phenethyl)-perylene-[3,4:9,10]bis(dicarboximide) (described in US 2007/0259475) in 12 ml dimethyl sulfoxide and 12 ml chlorobenzene was heated to 95° C. Then a solution of 0.13 g (1.6 mmol) sodium thiocyanate in 15 ml dimethyl sulfoxide was slowly added within one hour. The reaction solution was maintained at this temperature for 5 hours. After the reaction solution was cooled to room temperature chlorobenzene was removed by evaporation. 50 ml of water were added, whereby a precipitate was formed. The precipitate was filtered, washed with water and methanol and subsequently dried. The dark-red colored crude product was purified twice by chromatography on silica gel using toluene/ethyl acetate (20:1) as eluent. This yielded 0.11 g (24% of the theoretical amount) of a dark-red colored solid.

$^{1}$H-NMR (400 MHz, CD$_2$Cl$_2$): δ=9.09 (s, 2H), 8.80 (d, 2H), 8.47 (d, 2H), 7.10-7.42 (m, 10H), 4.45 (t, 4H), 3.08 (t, 4H) ppm.

Example 4

Example 4a

Preparation of N,N'-Bis(1-methylpentyl)-1,7(6)-dibromo-perylene[3,4:9,10]-bis(dicarboximide)

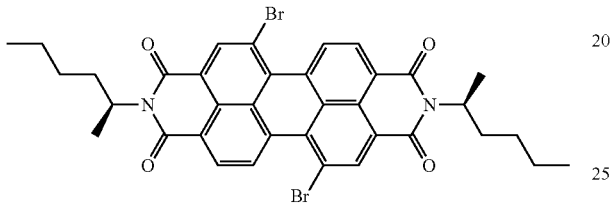

A suspension of 8.03 g (14.6 mmol) 1,7(6)-dibromo-perylene[3,4:9,10]tetracarbonic acid dianhydride (mixture of 1,7- and 1,6-Dibromo isomers) [described in DE 19547209] and 3.12 g (30.8 mmol) (S)-(+)-2-aminohexane in 120 ml anhydrous 1,4-dioxane was heated to 160° C. in a Roth reactor and maintained at that temperature for 1 hour while stirring continuously. After the reaction solution was cooled to room temperature 450 ml methanol were added. The mixture was stirred for 5 hours. The precipitate was filtered, washed with methanol and subsequently dried. The dark-red colored crude product was purified by chromatography on silica gel using dichloromethane as eluent. This yielded 5.24 g (50% of the theoretical amount) of a dark-red colored solid $^{1}$H-NMR (400 MHz, CDCl$_3$): δ=9.48 (d, 2H), 8.90 (s, 2H), 8.69 (d, 2H), 5.28 (m, 2H), 2.24 (m, 2H), 1.92 (m, 2H), 1.60 (m, 6H), 1.35 (m, 6H), 1.25 (m, 2H), 0.87 (t, 6H) ppm.

Example 4b

Preparation of N,N'-Bis(1-methylpentyl)-1,7(6)-dithiocyanato-perylene[3,4:9,10]-bis(dicarboximide)

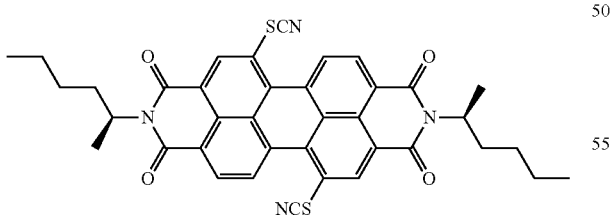

To a solution of 0.50 g (0.70 mmol) N,N'-bis(1-methylpentyl)-1,7(6)-dibromo-perylene[3,4:9,10]bis(dicarboximide) in 25 ml dimethyl sulfoxide was added within 1.5 hours a solution of 0.12 g (1.5 mmol) sodium thiocyanate in 10 ml dimethyl sulfoxide at 95° C. while stirring continuously. The solution was stirred for another 21 hours at 95° C. and cooled to room temperature. Then 150 ml water were added to the solution, whereby a precipitate was formed. The precipitate was filtered, washed with water and methanol and subsequently dried. The dark-red colored crude product was purified by chromatography on silica gel using dichloromethane as eluent. This yielded 0.30 g (64% of the theoretical amount) dark-red colored solid. The proportion of the 1,6-dithiocyanato isomer was 11% according to $^{1}$H NMR spectroscopy.

$^{1}$H NMR (500 MHz, CDCl$_3$) of the 1,7-dithiocyanato isomer: δ=9.10 (s, 2H), 8.80 (d, 2H), 8.47 (d, 2H), 5.29 (m, 2H), 2.23 (m, 2H), 1.94 (m, 2H), 1.61 (m, 6H), 1.35 (m, 6H), 1.25 (m, 2H), 0.88 (t, 6H) ppm.

$^{1}$H NMR (500 MHz, CDCl$_3$) of the 1,6-dithiocyanato isomer: δ=9.12 (s, 2H), 8.81 (d, 2H), 8.40 (d, 2H) ppm; only the signals in the aromatic region could be assigned.

The pure 1,7-dithiocyanato isomer with a melting point of 229-230° C. (decomposition from 225° C.) could be obtained by recrystallization from isopropanol.

Example 5

Preparation of a mixture of 2,6(7)-dichloro- and 2,6,7-trichloro-N,N'-bis(1H,1H-perfluorbutyl)-naphthalene[1,8:4,5]-bis(dicarboximide)

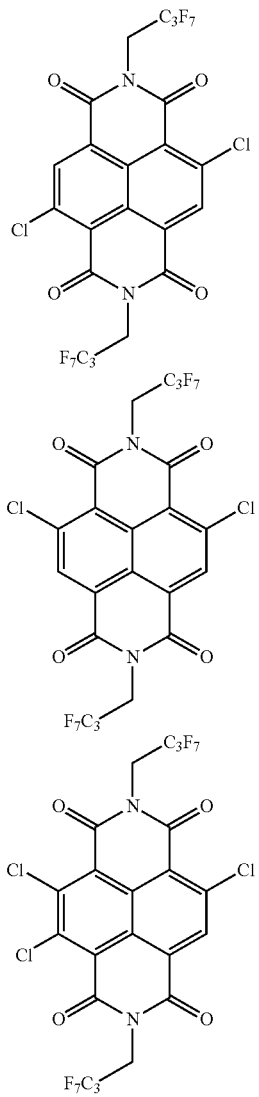

To a solution of 0.50 g (0.79 mmol) N,N'-bis(1H,1H-perfluorobutyl)naphthalene[1,8:4,5]-bis(dicarboximide), described in H. E. Katz et al., Materials Research Society Symposium Proceedings (2002), 665 (Electronics, Optical and Optoelectronic Polymers and Oligomers), 271-280, in 60 ml of 95-97 wt.-% sulfuric acid were added 1.06 g (5.4 mmol) of N,N''-dichloro-isocyanuric acid. After stirring for 30 min at room temperature, the solution was heated to 85° C. and maintained for 24 h at this temperature. The reaction solution was cooled to room temperature and diluted with 1 l of ice water, whereby a yellow solid precipitated. The suspension was stirred for 1 h and then neutralized with diluted NaOH. The solid was separated by a glas frit and washed with warm water. To the dry solid, methylene chloride was added. The yellow solution was filtered and evaporated to dryness. The residue was dried and purified by chromatography using silica gel and methylene chloride/cyclohexane (65:35) as mobile phase. Two main fractions were obtained and each evaporated and concentrated to give yellow solids. One fraction of 0.18 g (33% of the theoretical amount) contained 50% by weight of the trichloro-compound and 50% by weight of the two isomeric dichloro-compounds, according to $^1$H-NMR data. The other fraction of 0.070 g (13% of the theoretical amount) contained 66% by weight of the trichloro-compound and 34% by weight of the two isomeric dichloro-compounds, according to $^1$H-NMR data.

Example 6

Fabrication of Vapor-Deposited OFETs a) General Procedure for the Fabrication of Vapor-Deposited OFETs in the Top-Contact Configuration Highly doped p-type silicon (100) wafers (0.01-0.02 Ω·cm) were used as substrates A. Highly doped p-type silicon (100) wafers (0.005-0.02 Ω·cm) with a 100 nm thick thermally grown $SiO_2$ layer (capacitance 34 nF/cm$^2$) were used as substrates B.

Onto substrates A, a 30 nm thick layer of aluminum is deposited by thermal evaporation in a Leybold UNIVEX 300 vacuum evaporator from a tungsten wire, at a pressure of $2\times10^{-6}$ mbar and with an evaporation rate of 1 nm/s. The surface of the aluminum layer is oxidized by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of $C_{14}H_{29}PO(OH)_2$ [TDPA] or 1 mMol solution of $C_7F_{15}C_{11}H_{22}PO(OH)_2$ [FODPA]) and left in the solution for 1 hour, which results in the formation of a self-assembled monolayer (SAM) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the $AlO_x$/SAM gate dielectric on substrate A is 810 nF/cm$^2$ in case of $C_{14}H_{29}PO(OH)_2$ and 710 nF/cm$^2$ in case of $C_7F_{15}C_{11}H_{22}PO(OH)_2$. On substrates B, an about 8 nm thick layer of $Al_2O_3$ is deposited by atomic layer deposition in a Cambridge NanoTech Savannah (80 cycles at a substrate temperature of 250° C.). The surface of the aluminum oxide layer is activated by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of $C_{14}H_{29}PO(OH)_2$ [TDPA] or 1 mMol solution of $C_7F_{15}C_{11}H_{22}PO(OH)_2$ [FODPA]) and left in the solution for 1 hour, which results in the formation of a self-assembled monolayer (SAM) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the $SiO_2$/$AlO_x$/SAM gate dielectric on substrate B is 32 nF/cm$^2$ (independent on the choice of the phosphonic acid).

The contact angle of water on the TDPA-treated substrates is 108°, and on the FODPA-treated substrates 118°.

A 30 nm thick film of the organic semiconductor is deposited by thermal sublimation in a Leybold UNIVEX 300 vacuum evaporator from a molybdenum boat, at a pressure of $2\times10^{-6}$ mbar and with an evaporation rate of 0.3 nm/s.

For the source and drain contacts 30 nm of gold is evaporated through a shadow mask in a Leybold UNIVEX 300 vacuum evaporator from tungsten boat, at a pressure of $2\times10^{-6}$ mbar and with an evaporation rate of 0.3 nm/s. The transistors have a channel length (L) ranging from 10 to 100 μm and a channel width (W) ranging from 50 to 1000 μm.

To be able to contact the back side of the silicon wafer, the wafer (which also serves as the gate electrode of the transistors) is scratched on the back side and coated with silver ink.

The electrical characteristics of the transistors are measured on a Micromanipulator 6200 probe station using an Agilent 4156C semiconductor parameter analyzer. All measurements are performed in air at room temperature. The probe needles are brought into contact with the source and drain contacts of the transistors by putting them down carefully on top of the gold contacts. The gate electrode is contacted through the metal substrate holder onto which the wafer is placed during the measurements.

To obtain the transfer curve the drain-source voltage ($V_{DS}$) is held to 3 V (in case of substrate A) or 40 V (in case of substrate B). The gate-source voltage $V_{GS}$ is swept at medium speed from 0 to 3 V in steps of 0.03 V (substrate A) or from 0 to 40 V in steps of 0.4 V (substrate B) and back. The charge-carrier mobility is extracted in the saturation regime from the slope of $(I_D)^{1/2}$ versus $V_{GS}$.

To obtain the output characteristics the drain-source voltage ($V_{DS}$) is swept at medium speed from 0 to 3 V in steps of 0.03 V (substrate A) and from 0 to 40 V in steps of 0.4 V (substrate B), while the gate-source voltage $V_{GS}$ is held at up to 8 different voltages (e.g. 0, 0.5, 1, 1.5, 2, 2.5, 3 V in case of substrate A or 0, 10, 20, 30, 40 V in case of substrate B). Exemplary plots are given in FIGS. 2a-2c for the compound of example 1b and in FIGS. 2d and 2e for the compound of example 4b.

b) Table 1 gives the field-effect mobilities (μ) and on/off ratios ($I_{on}/I_{off}$) for compounds of example 1b and 4b with a thin (substrate A) and a thick (substrate B) gate dielectric with $C_{14}H_{29}PO(OH)_2$ (TDPA) for the SAM at a certain substrate temperature ($T_{sub}$) measured in ambient air.

TABLE 1

| Compound from example | Substrate | Substrate temperature $T_{sub}$ [° C.] | Electron mobility μ [cm$^2$/Vs] | On/off ratio $I_{on}/I_{off}$ |
|---|---|---|---|---|
| 1b | A | 110 | 0.051 | 10$^5$ |
| 4b | B | 70 | $1.9 \cdot 10^{-6}$ | n.d. |

Example 7

Procedure for a solution-processed OFET with the compound of example 3 on a standard substrate in the bottom-gate bottom-contact configuration A 0.5% solution of the compound of example 3 in chloroform warmed to 50° C. was spincoated (Spin Coater: Primus STT15) on an untreated standard silicium substrate at 5000 rpm. The standard silicium substrate consisted of a silicium wafer with a 230 nm thick siliciumdioxid layer ($\epsilon_r$=3.9) and D/S contacts with gold (30 nm) and ITO as an adhesive.

The electrical characteristics of the transistor was measured with an Agilent 4155C Semiconductor Parameter Analyzer. The transistor had a channel length (W) of 10 mm and a channel width (L) of 10 μm. All measurements were performed in air at room temperature.

To obtain the transfer curve the drain-source voltage ($U_{DS}$) is held to 40 V. The gate-source voltage $U_{GS}$ is swept at medium speed from −20 to 40 V in steps of 2 V and back. The charge-carrier mobility is extracted in the saturation regime from the slope of $(I_D)^{1/2}$ versus $V_{GS}$. The respective plot is shown in FIG. 3b.

To obtain the output characteristics the drain-source voltage ($V_{DS}$) is swept at medium speed from 0 to 40 V in steps of 2 V, while the gate-source voltage $V_{is}$ is held at up to 4 different voltages (10, 20, 30, 40 V). The respective plot is shown in FIG. 3a.

An electron mobility of $\mu$=1.7×10$^{-6}$ cm$^2$/Vs and an on/off ratio of 2.4×10$^3$ were obtained.

The invention claimed is:

1. A compound of formula I:

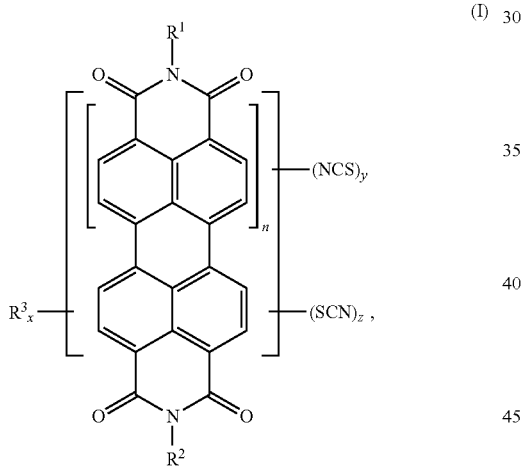

wherein:
R$^1$ and R$^2$, at each occurrence, are independently H, a C$_{1-30}$ alkyl group, a C$_{2-30}$ alkenyl group, a C$_{2-30}$ alkynyl group, a C$_{1-30}$ haloalkyl group, or a 3-22 membered cyclic moiety, each optionally substituted with 1-4 groups independently selected from the group consisting of halogen, —CN, —NO$_2$, —C(O)H, —C(O)OH, —CONH$_2$, —OH, —NH$_2$, —CO(C$_{1-14}$ alkyl), —C(O)OC$_{1-14}$ alkyl, —CONH(C$_{1-14}$ alkyl), —CON(C$_{1-14}$ alkyl)$_2$, —S—C$_{1-14}$ alkyl, —O—(CH$_2$CH$_2$O)$_n$(C$_{1-14}$ alkyl), —NH(C$_{1-14}$ alkyl), —N(C$_{1-14}$ alkyl)$_2$, a C$_{1-14}$ alkyl group, a C$_{2-14}$ alkenyl group, a C$_{2-14}$ alkynyl group, a C$_{1-14}$ haloalkyl group, a C$_{1-14}$ alkoxy group, a C$_{6-14}$ aryl group, a C$_{3-14}$ cycloalkyl group, a 3-14 membered cycloheteroalkyl group, and a 5-14 membered heteroaryl group;
each R$^3$ is independently a halogen, —CN, —NO$_2$, —C(O)O(C$_{1-14}$ alkyl), —C(O)O(C$_{6-14}$ aryl), —CHO, C$_{1-14}$ alkylsulfon, C$_{6-14}$ arylsulfon, a sulfonic acid C$_{1-14}$ alkylester or C$_{6-14}$ arylester group, —CONH$_2$, —CONH(C$_{1-14}$ alkyl), —CONH(C$_{6-14}$ aryl), —CON(C$_{1-14}$ alky)$_2$, —CON(C$_{1-14}$ alkyl)(C$_{6-14}$ aryl), —CON(C$_{6-14}$ aryl)$_2$, —C(O)H, a C$_{1-14}$ alkoxy group, a C$_{1-14}$ alkylthio group, a C$_{6-14}$ aryloxy group, a C$_{6-14}$ arylthio group, a C$_{1-14}$ alkyl group, a 3-14 membered cycloheteroalkyl group, a C$_{6-20}$ aryl group, or a 5-20 membered heteroaryl group;
n is 0, 1, 2, or 3;
x is 0, 1, 2, 3, or 4;
y is 1, 2, 3, or 4 if z is 0, and is 0, 1, 2, 3, or 4 if z is >0; and
z is 1, 2, 3, or 4 if y is 0, and is 0, 1, 2, 3, or 4 if y is >0.

2. The compound of claim 1, wherein R$^1$ and R$^2$, at each occurrence, are independently a C$_{1-12}$ alkyl group, a C$_{1-12}$ haloalkyl group, or a C$_{7-20}$ arylalkyl group.

3. The compound of claim 1, wherein R$^1$ and R$^2$, at each occurrence, are independently a C$_{1-12}$ alkyl group, a C$_{1-12}$ fluoroalkyl group, or a C$_{7-12}$ phenylalkyl group, wherein the phenyl is optionally substituted with 1-5 halogen atoms.

4. The compound of claim 1, wherein n=0.

5. The compound of claim 1, wherein n=1.

6. The compound of claim 1, wherein x=0, y=0, and z=2.

7. The compound of claim 1, wherein x=0, y=1, and z=1.

8. The compound of claim 1, wherein x=0, y=2, and z=0.

9. The compound of claim 1, having formula Ia, Ib, or Ic:

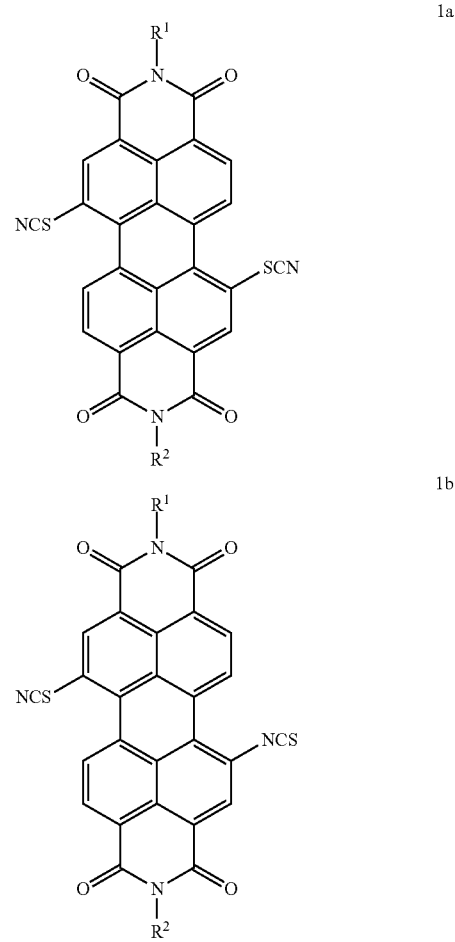

10. The compound of claim 1, having formula Id, Ie, or If:

1c
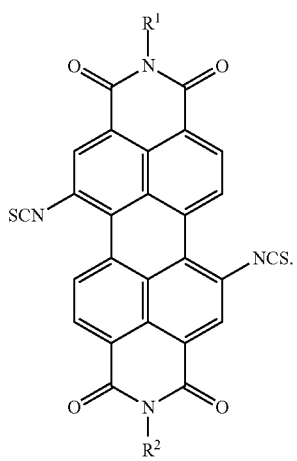

1d
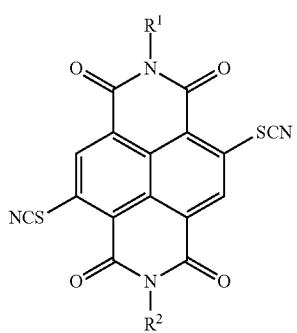

1e
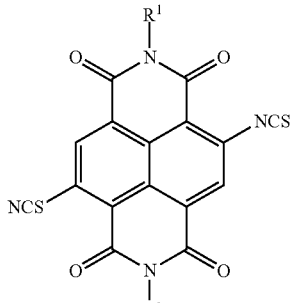

1f
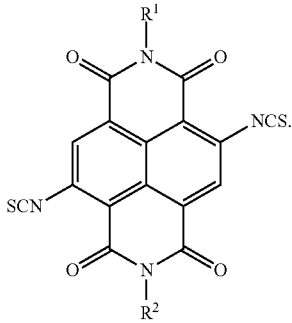

11. A thin film semiconductor, comprising a compound of claim 1.

12. A field effect transistor device, comprising the thin film semiconductor of claim 11.

13. A photovoltaic device, comprising the thin film semiconductor of claim 11.

14. An organic light emitting diode device, comprising the thin film semiconductor of claim 11.

15. A unipolar or complementary circuit device, comprising the thin film semiconductor of claim 11.

* * * * *